US007682346B2

(12) United States Patent
McNally et al.

(10) Patent No.: US 7,682,346 B2
(45) Date of Patent: Mar. 23, 2010

(54) LOW-PROFILE ENTEROSTOMY DEVICE

(75) Inventors: David J. McNally, Sandy, UT (US); Alejandro Flores, West Newton, MA (US)

(73) Assignee: Zevex, Inc., Salt Lake City, UT (US)

( * ) Notice: Subject to any disclaimer, the term of this patent is extended or adjusted under 35 U.S.C. 154(b) by 1209 days.

(21) Appl. No.: 10/881,744

(22) Filed: Jun. 30, 2004

(65) Prior Publication Data

US 2005/0004540 A1 Jan. 6, 2005

Related U.S. Application Data

(63) Continuation of application No. 10/016,669, filed on Dec. 10, 2001, now Pat. No. 6,902,541, which is a continuation of application No. 09/507,141, filed on Feb. 18, 2000, now Pat. No. 6,328,720.

(51) Int. Cl.
*A61M 1/00* (2006.01)

(52) U.S. Cl. .......................... 604/332; 604/32; 604/910

(58) Field of Classification Search ................. 604/910, 604/32, 335, 248, 101.03, 332, 334, 338
See application file for complete search history.

(56) References Cited

U.S. PATENT DOCUMENTS

| | | | | |
|---|---|---|---|---|
| 3,050,066 | A | 8/1962 | Koehn | |
| 3,915,171 | A | 10/1975 | Shermeta | |
| RE29,207 | E | 5/1977 | Bolduc et al. | |
| 4,315,513 | A | 2/1982 | Nawash et al. | |
| 4,356,824 | A | 11/1982 | Vazquez | |
| 4,509,514 | A | 4/1985 | Brain | |
| 4,555,242 | A | 11/1985 | Saudagar | |
| 4,575,371 | A | 3/1986 | Nordqvist et al. | |
| 4,654,027 | A | 3/1987 | Dragan et al. | |
| 4,798,592 | A | 1/1989 | Parks | |
| 4,813,935 | A | 3/1989 | Haber et al. | |
| 4,848,343 | A | 7/1989 | Wallsten et al. | |
| 4,850,953 | A * | 7/1989 | Haber et al. | 600/32 |
| 4,861,334 | A | 8/1989 | Nawaz | |
| 4,927,412 | A | 5/1990 | Menasche | |
| 4,976,710 | A | 12/1990 | Mackin | |
| 5,074,845 | A | 12/1991 | Miraki et al. | |
| 5,080,650 | A | 1/1992 | Hirsch et al. | |
| 5,125,897 | A | 6/1992 | Quinn et al. | |
| 5,154,725 | A | 10/1992 | Leopold | |
| 5,171,222 | A | 12/1992 | Euteneuer et al. | |
| 5,203,769 | A | 4/1993 | Clement et al. | |
| 5,207,641 | A * | 5/1993 | Allton | 604/32 |
| 5,226,889 | A | 7/1993 | Sheiban | |

(Continued)

*Primary Examiner*—Nicholas D Lucchesi
*Assistant Examiner*—Laura A Bouchelle
(74) *Attorney, Agent, or Firm*—Bateman IP Law Group

(57) ABSTRACT

An enterostomy device for providing fluids and nutrients through a stoma formed through the abdominal wall of a patient is described. The enterostomy device, which may be configured as either a gastrostomy device or a jejunostomy device, comprises a low-profile retaining member which is configured to be unobtrusively positioned within the stomach or the intestine, and which is configured to provide sufficient surface area for contacting the stomach or intestine to prevent unintentional removal or release of the enterostomy device from the patient. The enterostomy device is also structured with a low-profile port hub for facilitating the inflation of the retaining member and feeding and venting through the stoma.

25 Claims, 7 Drawing Sheets

U.S. PATENT DOCUMENTS

| | | | | | |
|---|---|---|---|---|---|
| 5,261,879 | A | | 11/1993 | Brill | |
| 5,308,325 | A | | 5/1994 | Quinn et al. | |
| 5,336,203 | A | | 8/1994 | Goldhardt et al. | |
| 5,342,321 | A | | 8/1994 | Potter | |
| D350,393 | S | | 9/1994 | Potter | |
| 5,350,362 | A | | 9/1994 | Stouder, Jr. | |
| 5,356,391 | A | | 10/1994 | Stewart | |
| 5,358,488 | A | * | 10/1994 | Suriyapa | 604/103.03 |
| 5,391,159 | A | | 2/1995 | Hirsch et al. | |
| 5,403,290 | A | | 4/1995 | Noble | |
| 5,411,491 | A | | 5/1995 | Goldhardt et al. | |
| 5,413,565 | A | | 5/1995 | Michels et al. | |
| 5,458,583 | A | | 10/1995 | McNeely et al. | |
| 5,549,657 | A | | 8/1996 | Stern et al. | |
| 5,556,385 | A | | 9/1996 | Andersen | |
| 5,718,691 | A | | 2/1998 | Russo | |
| 5,769,816 | A | | 6/1998 | Barbut et al. | |
| 5,800,408 | A | | 9/1998 | Strauss et al. | |
| 5,836,924 | A | * | 11/1998 | Kelliher et al. | 604/248 |
| 5,865,816 | A | | 2/1999 | Quinn | |
| 5,997,503 | A | | 12/1999 | Willis et al. | |
| 5,997,546 | A | | 12/1999 | Foster et al. | |
| 6,007,521 | A | | 12/1999 | Bidwell et al. | |
| 6,019,746 | A | | 2/2000 | Picha et al. | |
| 6,328,720 | B1 | * | 12/2001 | McNally et al. | 604/332 |
| 6,902,541 | B2 | * | 6/2005 | McNally et al. | 604/32 |

* cited by examiner

LOW-PROFILE ENTEROSTOMY DEVICE

RELATED APPLICATIONS

This application is a continuation of U.S. patent application Ser. No. 10/016,669 file Dec. 10, 2001, now U.S. Pat. No. 6,902,541, which was a continuation of U.S. patent application Ser. No. 09/507,141, filed Feb. 18, 2000, now U.S. Pat. No. 6,328,720.

BACKGROUND OF THE INVENTION

1. Field of the Invention

This invention relates to medical devices for use with humans and animals, and specifically relates to enterostomy devices for insertion in the stomach or intestine to provide delivery of nutrients and other substances directly to the gastrointestinal tract of patients who cannot be fed by other conventional means.

2. Statement of the Art

It frequently becomes necessary in the medical treatment of humans and animals to provide nutrients or other substances to the patient's stomach by means other than the mouth due to the existence of some condition in, or relative to, the mouth or esophagus which renders impossible the normal intake of fluids or nutrients through the mouth. Such conditions may include, for example, a localized disease condition of the mouth or esophagus or the inability of the patient to chew or swallow. Delivery of fluids or nutrients to the patient's stomach may be provided in one of three generally-recognized methods—namely nasoenteric tube placement, gastrostomy or jejunostomy. Feeding via nasoenteric tube involves the positioning of one or more tubes through the patient's nostrils, through the nasal passages to the throat and down the esophagus to the stomach. Gastrostomy involves the formation of a stoma, or opening, through the patient's abdominal wall and stomach, followed by placement of a tube through the stoma for delivery of fluids and nutrients directly to the stomach. Jejunostomy involves the formation of a stoma through the lower abdominal wall and the intestine, followed by the insertion of a tube through the stoma and into the intestinal tract.

Each type of feeding identified above has its appropriate applications and contraindications. For example, nasoenteric tube insertion is suitable for temporary or short term feeding requirements, but is unsuitable where the patient cannot tolerate the placement of such tubes or where feeding must be continued for longer than a week or two. Gastrostomy is appropriate for longer periods of required feeding (e.g., more than four weeks) and has the particular advantage of using the stomach's storage capacity, osmotic regulation and prolongation of intestinal transit to maximize the intake of nutrients. Gastrostomy, however, may not be suitable where the stomach is in a diseased condition, where there is abnormal gastric emptying, significant esophogeal reflux or lack of inherent gag reflex in the patient. Jejunostomy is appropriate where gastrostomy is contraindicated by one of the aforementioned conditions, but is less desirable than gastrostomy because of the shortened period of time that the nutrients may be absorbed by the intestinal tract.

A number of gastrostomy and jejunostomy devices have been developed over the years to supply a fluid-communications port to the stomach or intestine. Examples of gastrostomy and jejunostomy devices are disclosed in U.S. Pat. No. 5,549,657 to Stern, et al.; U.S. Pat. No. 5,411,491 to Goldhardt, et al.; U.S. Pat. No. 5,391,159 to Hirsch, et al.; U.S. Pat. No. 5,356,391 to Stewart; U.S. Pat. No. 5,342,321 to Potter; U.S. Pat. No. 5,336,203 to Goldhardt, et al.; U.S. Pat. No. 5,080,650 to Hirsch, et al.; U.S. Pat. No. 4,861,334 to Nawaz; U.S. Pat. No. 4,850,953 to Haber, et al., and U.S. Pat. No. 3,915,171 to Shermata.

Previously disclosed enterostomy devices are generally configured in a similar manner to deliver nutrients to the stomach or intestine. Specifically, they comprise a tube which is positionable through a stoma or opening formed through the patient's abdominal wall and stomach or intestine, a retainer device positioned at one end of the tube which is located within the stomach or intestine, and a valve device positioned at the end of the tube opposite the retainer device. The valve device provides at least one opening through which fluid can be introduced to flow through the tube. The valve device may also serve to maintain the tube in position within the stoma and often provides a means by which the tube may later be removed from the stoma.

The retainer devices of previously disclosed gastrostomy devices generally function well for their intended purpose (i.e., anchoring the gastrostomy device to the stomach or intestinal lining and delivery of substances to the gastrointestinal tract), but they are almost uniformly rendered disadvantageous in being large or potentially obstructive in configuration. That is, the design or configuration of the retainer device of most known gastrostomy devices is such that it extends a significant distance into the lumen of the stomach or intestine, thereby causing an obstruction of the stomach or intestine, or the retention device extends so far into the stomach or intestine that it contacts tissue on the opposing side of the stomach or intestine causing irritation or infection. Further, the configuration of some known devices provides an insufficient surface area for contact with the stomach or intestine lining, which can result in dislodgement and accidental removal or expulsion of the gastrostomy device from the patient's body. Additionally, most gastrostomy devices provide an aperture, in axial alignment with the feed tube of the device, through which nutrients are feed and, oftentimes, through which fluids are vented from the stomach or intestine. To prevent entry of infectious agents or accidental release of fluids from the stomach or intestine through the gastrostomy device, many known devices provide a tethered plug which can be inserted into the aperture. In such devices, trauma to the stoma occurs when a syringe or tube set is inserted in the axially-aligned aperture and trauma also occurs to the stoma when the plug in inserted and removed from the aperture.

Thus, it would be advantageous to provide an enterostomy device which is structured to provide a retaining member having an increased area of contact with the stomach or intestinal lining, thereby preventing premature or unintended release of the device from the patient, and one which is unobstructive in configuration to prevent blockage in the stomach or intestine. It would further be advantageous to provide a enterostomy device which is structured with a low-profile valved hub which eliminates trauma imposed on the stoma as is typically experienced with known gastrostomy devices.

SUMMARY OF THE INVENTION

In accordance with the present invention, an enterostomy device is configured to provide a low-profile retaining member positionable within the stomach or intestine of a patient to prevent obstruction of the patient's gastrointestinal tract while providing sufficient contact between the retaining member and the gastrointestinal tract to prevent dislodgement of the device from the patient. The enterostomy device of the present invention is also structured with a port hub having a low profile to facilitate inflation of the retention member, feeding through the gastrostomy device and venting of fluids through the gastrostomy device while preventing trauma to the stoma. The enterostomy device is structured to be easily deployable through an existing stoma and provides an inflatable retaining member which is easily deployed within the stomach or intestine. The enterostomy device of the present invention is suitable for use with both human and animal patients, but is described herein with respect to use in humans as one exemplar application.

The enterostomy device of the present invention is adaptable for use as either a gastrostomy device or a jejunostomy device. In either application, the enterostomy device comprises a stoma tube having a first end positionable toward the outside of the patient's body (also referred to as the proximal end) and a second end positionable within the patient's body (also referred to as the distal end). At least one opening is generally located at the first, or proximal end, of the stoma tube which enables the introduction of fluid or other substances into the stoma tube. A low-profile retaining member is located at the second, or distal, end of the stoma tube and is positionable within the patient's body. The retaining member is generally structured with an increased surface area for contacting the lining of the stomach or intestine to assure that the enterostomy device cannot be accidentally removed.

The retaining member is generally structured as a flattened inflatable ring which extends outward from the stoma tube at the distal end thereof. The flattened profile of the retaining member and the distance it extends from the stoma tube provide an increased surface area for contacting the stomach or intestinal lining about the stoma to thereby prevent accidental dislodgement or removal of the enterostomy device from the stoma. The inflatable ring of the retaining member is in fluid communication with an inflation line incorporated into the stoma tube and is structured to receive a fluid, either gas or liquid, from the inflation line to inflate the ring. For example, the stoma tube may be structured with a valved chamber through which an inflation fluid is injectable to inflate the ring. Upon inflation, the inflatable ring extends outward from the distal end of the stoma tube in an plane generally perpendicular to the longitudinal axis of the stoma tube. The retaining member is made of a biocompatible, flexible material, such as silicone or other suitable material, and is configured to prevent incorporation of the device into the surrounding stomach or intestinal lining.

The port hub located at the proximal end of the stoma tube is configured to be located on the outside of the patient's body and effectively encloses or covers the stoma to prevent leakage or infiltration of foreign matter through the stoma opening. The port hub also functions to provide means for ingress and egress of fluids through the stoma tube and is preferably structured with a means for closing off the stoma tube to thereby prevent the infiltration of unwanted matter or the escape of fluids through the stoma tube. The port hub is preferably configured to have a low profile as well, and is configured to rest against the patient's body in an unobtrusive manner so as not to be readily detectable under clothing. The configuration of the port hub may vary considerably, but is structured with at least one port through which substantially flowable fluids or nutrients can be introduced for delivery to the stomach or intestine via the stoma tube. In a preferred embodiment of the invention, the port hub includes at least one port through which a fluid or other substance may be injected. The axis of the port may generally be oriented normal to the axis of the stoma tube and may be placed in fluid communication therewith.

In one particularly preferred embodiment, the port hub is configured with a single port and is structured to be rotatable relative to the stoma tube so that the port can be selectively aligned with one or more openings leading into the stoma tube. The rotatable port hub can also be rotated to disengage the port from alignment with the opening or openings to the stoma tube to place the enterostomy device in a closed position. The configuration thus eliminates the need for tethered plugs. Furthermore, because the opening or openings into the stoma tube are normal (i.e., perpendicular) to the axis of the stoma tube, no pressure is applied to the axis of the stoma tube, as in prior devices, to cause trauma to the stoma. The rotatable port hub is particularly structured to provide easy access to the inflation line for inflating the retaining member and to access the port for feeding or venting through the stoma tube, and the design eliminates the need for bulky tube sets as are typically required with known gastrostomy devices, although the present invention is structured for accepting a tube set arrangement if desired.

In one embodiment, the enterostomy device of the present invention may be configured for use as a gastrostomy device for implantation through an existing stoma and into a patient's stomach. The gastrostomy device provides a low-profile retaining member positionable against the stomach wall to prevent obstruction of the interior of the stomach. In an alternative embodiment, the enterostomy device may be configured for use as a jejunostomy device for implantation through an existing stoma into a portion of the intestine. The jejunostomy device is structured to provide a low-profile retaining member positionable within the intestine which does not obstruct the interior of the intestine. Thus, materials may flow through the intestine and past the retaining member without being obstructed thereby. The jejunostomy device further includes a jejunostomy tube which extends from the distal end of the stoma tube to deliver fluids or other substances into the intestine.

BRIEF DESCRIPTION OF THE DRAWINGS

In the drawings, which illustrate what is currently considered to be the best mode for carrying out the invention.

DETAILED DESCRIPTION OF THE ILLUSTRATED EMBODIMENTS

Figure 1:
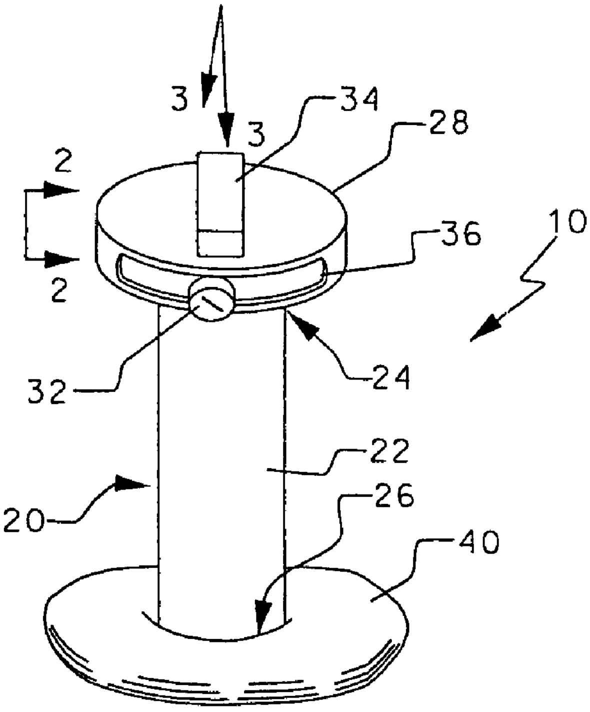
FIG. 1 is a perspective view of the enterostomy device of the present invention, prior to deployment in a pre-existing stoma, illustrating the inflation line and rotatable port hub.
Figure 2:
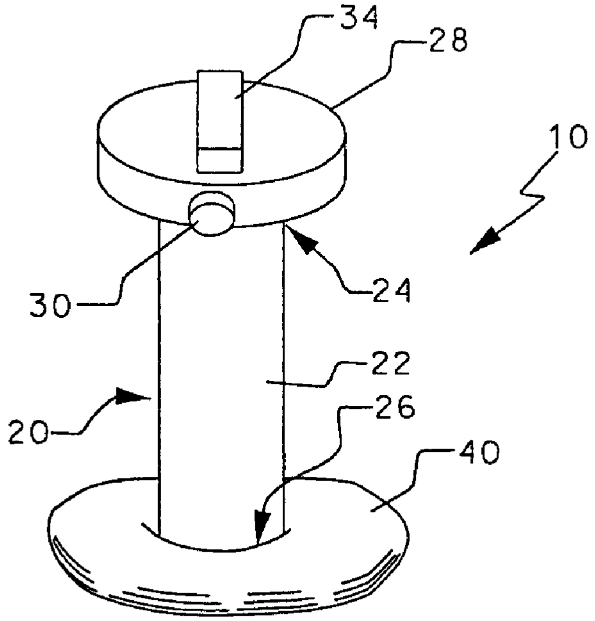
FIG. 2 is a perspective view of the enterostomy device shown in FIG. 1, rotated 180° to illustrate the port of the port hub.
Figure 13:
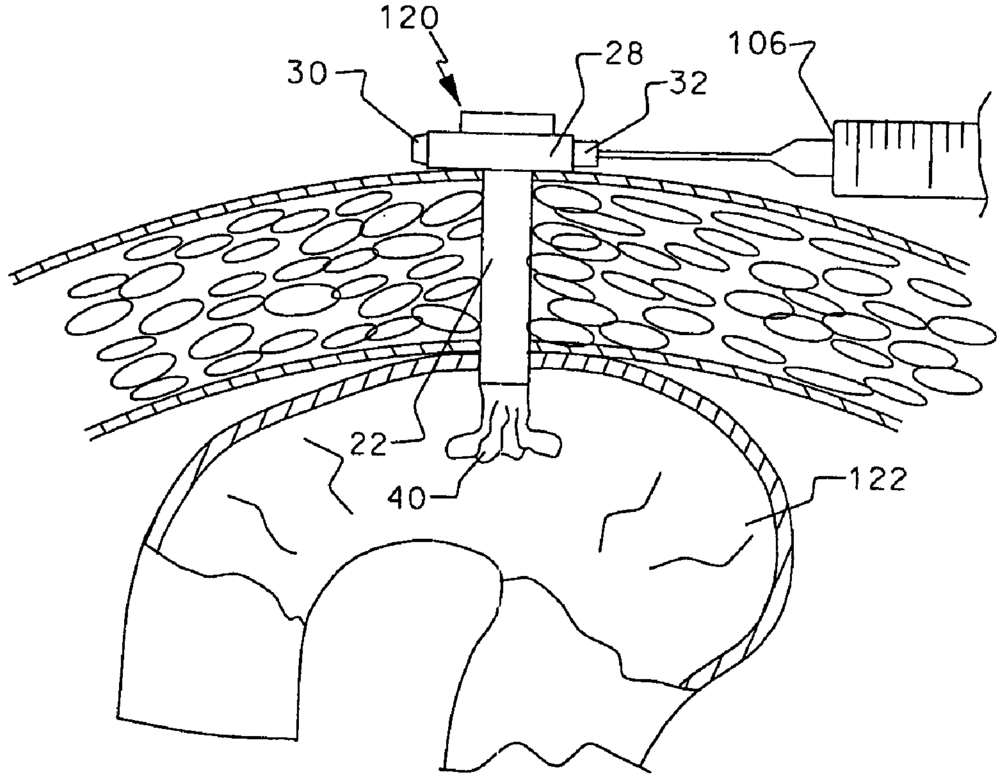
FIG. 13 is a view in partial cross section illustrating an alternative embodiment of the enterostomy device of the present invention configured for use as a jejunostomy device and being partially deployed in a patient's intestinal tract.
Figure 14:
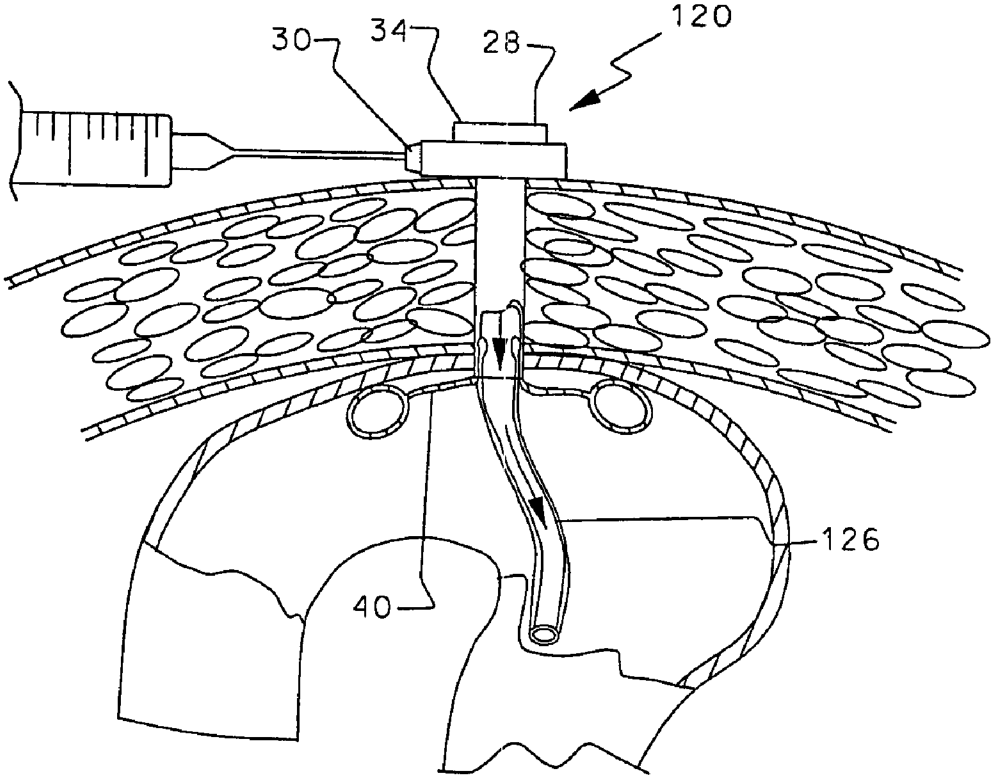
FIG. 14 is a view in partial cross section of the jejunostomy device illustrated in FIG. 13 as it may appear upon full deployment within the intestinal tract of a patient.

The general configuration of the enterostomy device 10 of the present invention is illustrated in FIGS. 1-7, where FIGS. 1 and 2 illustrate the device 10 in a pre-deployment mode. Further, FIGS. 1-11 illustrate the device 10 as it may be configured for use as a gastrostomy device 20 positionable within the stomach of a patient while FIGS. 13 and 14 illustrate the present invention as a jejunostomy device.

Referring to FIGS. 1 and 2, the gastrostomy device 20 generally comprises a stoma tube 22 having a first end 24, also referred to as the proximal end, positionable toward the outside of the patient's body and a second end 26, also referred to as the distal end, which is positionable within the patient's stomach. The circumferential and length dimensions of the stoma tube 22 may vary and are dictated by the length and inner diameter of the existing stoma formed through the patient's body. Therefore, in a medical setting, a gastrostomy device having the appropriate circumferential and length dimensions suitable for use with the given patient would be selected from an inventory of variably sized gastrostomy devices of the present invention.

As generally shown in FIGS. 1 and 2, a rotatable port hub 28 is located at the first end 24 of the stoma tube 22 to facilitate access to the stoma tube through a port 30 formed in the rotatable port hub 28. The rotatable port hub 28 is also configured to accommodate a valved inflation connector 32 which is formed with the stoma tube 22, as illustrated and described more fully below. The rotatable port hub 28 is rotatable by a handle 34 generally formed at the top of the rotatable port hub 28 and is configured with a slot 36 which permits rotation of the port hub 28 relative to the stoma tube 22 and the fixed inflation connector 32 of the stoma tube 22. As also shown generally in FIGS. 1 and 2, an inflatable retaining member 40 is located at the distal end 26 of the stoma tube 22 and extends outward therefrom.

Figure 4:
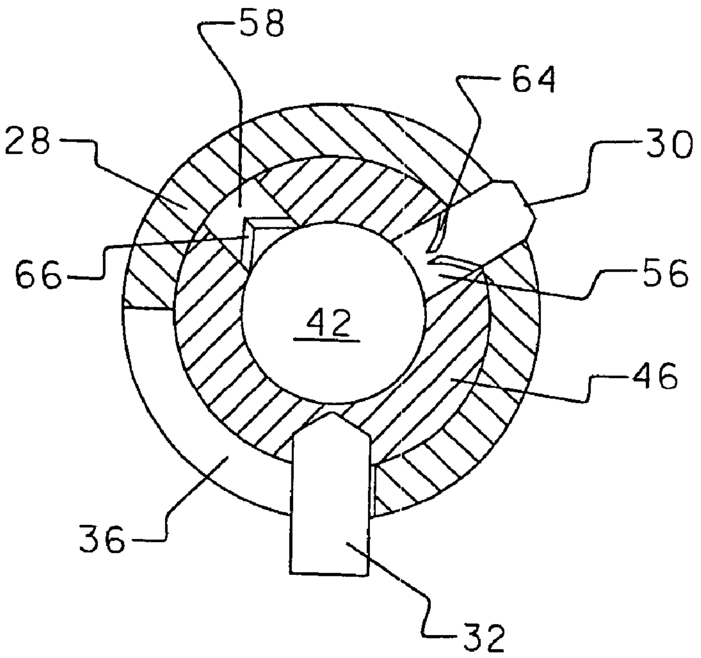
FIG. 4 is a view in lateral cross section of the enterostomy device shown in FIG. 1, taken at line 2-2, illustrating the port aligned with an inlet opening of the stoma tube.
Figure 5:
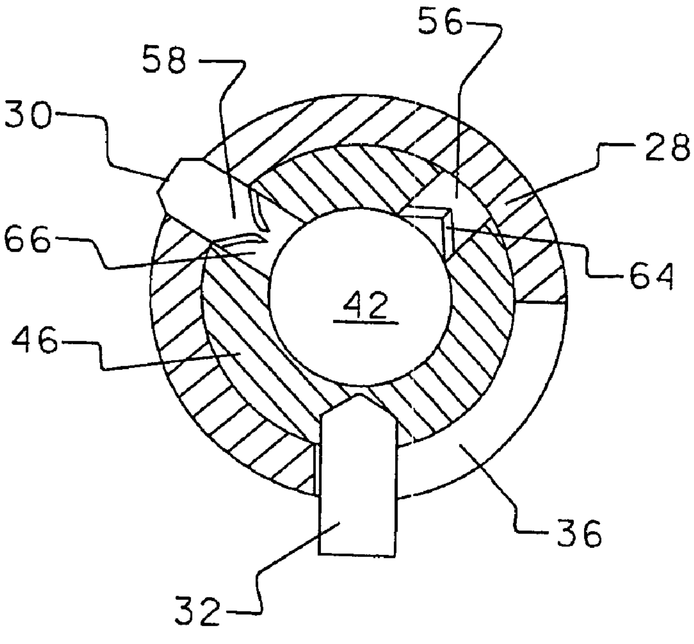
FIG. 5 is a view in lateral cross section of the enterostomy device shown in FIG. 1, taken at line 2-2, illustrating the port aligned with an outlet opening of the stoma tube.
Figure 6:
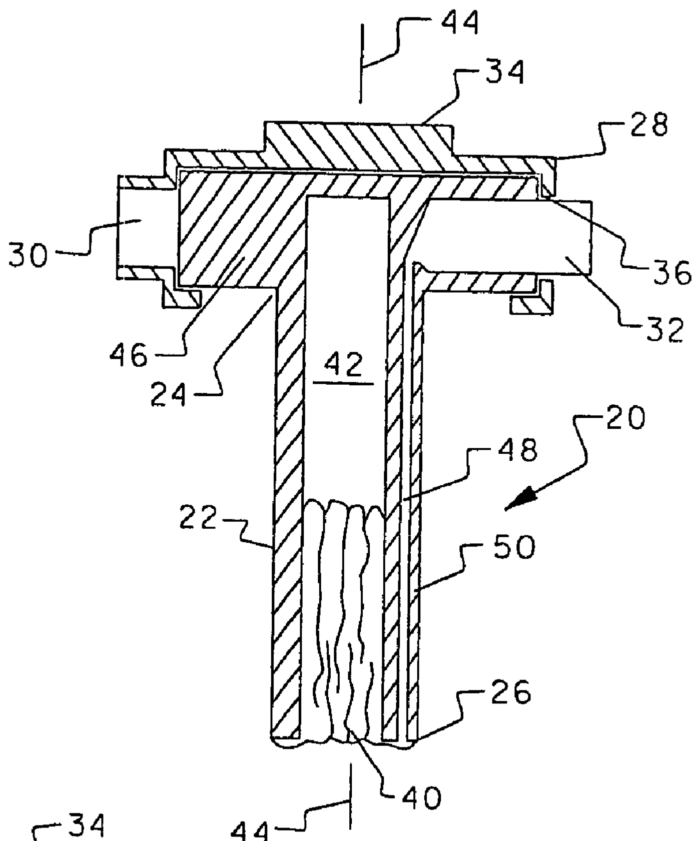
FIG. 6 is a view in longitudinal cross section of the enterostomy device shown in FIG. 1, taken at line 3-3, illustrating the rotatable port hub in a closed position and the retaining member in a pre-deployed orientation.

As shown and described more fully with reference to FIGS. 3-7, the stoma tube 22 has a central bore 42, formed about a central axis 44 (FIG. 6), which extends from the first end 24 to the second end 26 of the stoma tube 22. The first end 24 of the stoma tube 22 may be formed with an outward-extending flange 46 about which the rotatable port hub 28 is positioned and movable. As shown in FIG. 6, the inflation connector 32 is formed through the flange 46 of the stoma tube 22 and is in fluid communication with an inflation line 48 which extends through the wall 50 of the stoma tube 22. The inflation line 48 may be co-extensive, as shown, with the central bore 42 of the stoma tube 22 and is in fluid communication with the retaining member 40, shown inserted within the central bore 42 of the stoma tube 22 in a pre-deployment mode. The inflation connector 32 is structured in a conventional manner known in the art where a valve permits introduction of an inflation fluid, such as air or saline solution, through the valve and into the inflation line 48 for inflation of the retaining member 40. Any suitable valve structure may be employed in the inflation connector which retains the inflation fluid within the retaining member 40 until such time as the inflation fluid may be released from the retaining member 40 through the inflation line 48. Such devices are commonly known in the art and are not described further here.

Figure 3:
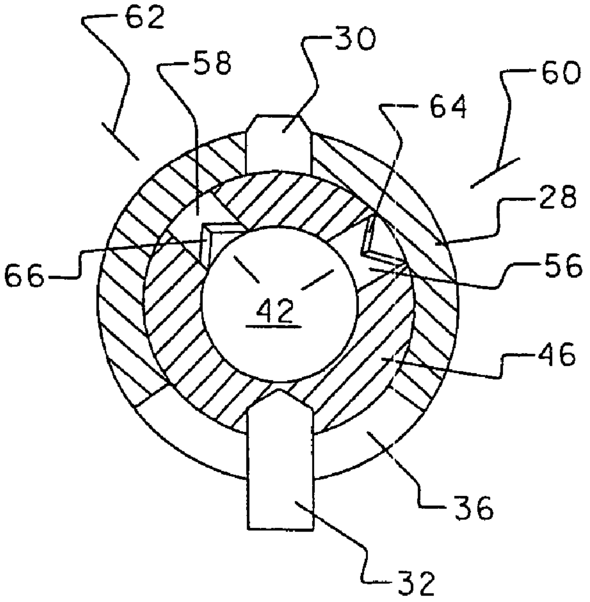
FIG. 3 is a view in lateral cross section of the enterostomy device shown in FIG. 1, taken at line 2-2, illustrating the rotatable port hub in a closed position.

As shown more fully in FIGS. 3-5, the rotatable port hub 28 may be selectively rotated relative to the flange 46 of the stoma tube 22 to align the port 30 with one or more openings formed through the flange 46 or to close the gastrostomy device 20 so that the central bore 42 is inaccessible from outside the body of the patient. That is, as shown in FIGS. 3-5, for example, two openings, comprising an inlet 56 and an outlet 58, may be formed through the flange 46 of the stoma tube 22, each having an axis 60, 62, respectively (FIG. 3), which is substantially perpendicular to the central axis 46 of the central bore 42. By "substantially perpendicular" is meant that the axis 60, 62 of one or both of the respective inlet 56 and outlet 58 may be angled upwardly relative to the central axis 44 of the stoma tube 22 and may, therefore, not be strictly perpendicular thereto. As shown in FIG. 3, the port hub 28 may be rotated so that the port 30 is not aligned with either the inlet 56 or the outlet 58 so that access to the central bore 42 is prevented. In such a position, the gastrostomy device 20 may be said to be in a closed position.

Figure 7:
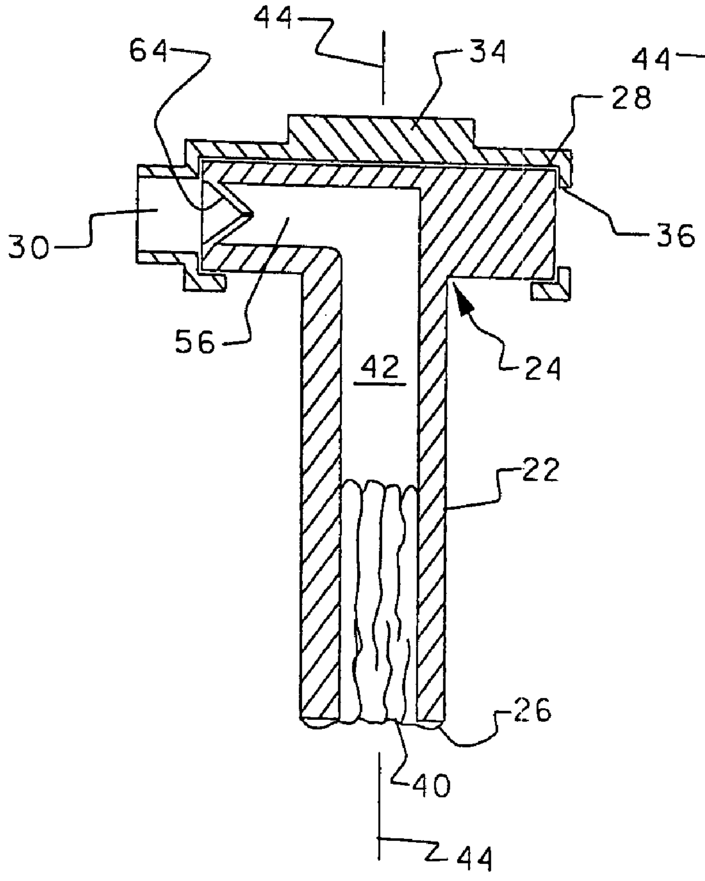
FIG. 7 is a view in longitudinal cross section of the enterostomy device shown in FIG. 1 where the rotatable port hub is aligned with the inlet opening and the retaining member is in a pre-deployment orientation.

As shown in FIGS. 4 and 7, the port hub 28 may be rotated relative to the stoma tube 22 to align the port 30 with the inlet 56 to thereby gain access to the central bore 42 of the stoma tube 22 for feeding the patient. The inlet 56 may preferably be configured with a valve 64, such as a one-way valve, which enables material to be introduced into the inlet without reflux of material out of the inlet. The valve 64 may, for example, be openable by the insertion of a male Luer connector into the port 30 through which the feeding material flows to the central bore 42. Rotation of the port hub 28 relative to the flange 46 of the stoma tube 22 and the fixed inflation connector 32 is accomplished by formation of a slot 36 in the rotatable port hub 28 through which the inflation connector 32 extends, as shown. It should be noted that the inflation connector 32 may be configured to extend a distance beyond the circumference of the port hub 28 to provide a graspable element which may be held while turning the handle 34 of the port hub 28 to assure stability of the stoma tube 22 during rotation of the port hub 28.

As shown in FIG. 5, the port hub 28 may also be rotated to align the port 30 with the outlet 58 for venting fluids, such as gas, from the patient's stomach. The outlet 58 may preferably be structured with a valve 66, such as a one-way valve, which allows fluids to escape from the stomach cavity, but does not allow matter from the environment external to the stomach to enter into, and possibly infect, the stomach. The valve 66 may, most suitably, be operable as a result of pressure differentials existing between the internal and external gastrointestinal environment. Obviously, when the port 30 is not aligned with the outlet 58, venting cannot occur. It should be noted that while simple flapper valves are shown representationally in FIGS. 3-5 and 7 as means for controlling the flow of fluids or other material into and out of the inlet 56 and outlet 58, respectively, any number of suitable valving devices may be employed to achieve the desired function, including, for example, ball valves or the like. Again, it can be seen in FIG. 5 that the existence of the slot 36 formed in the rotatable port hub 28 allows movement of the port hub 28 relative to the fixed inflation connector 32 formed in the flange 46 of the stoma tube 22.

Figure 8:
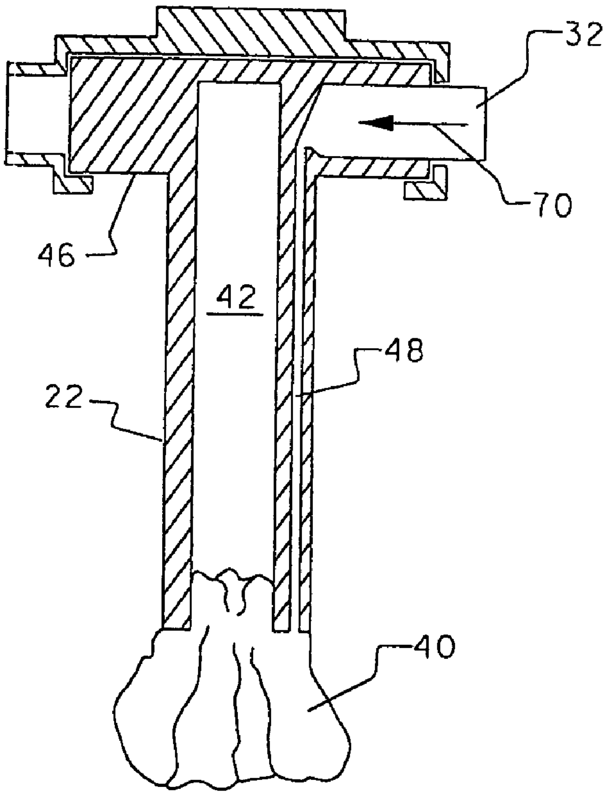
FIG. 8 is a view in lateral cross section of the enterostomy device illustrating the retaining member in a partially deployed position.

FIG. 6 illustrates, in one exemplar embodiment of the invention, how the retaining member 40 is located within the central bore 42 of the stoma tube 42 prior to deployment of the gastrostomy device 20 in the patient's stomach. FIG. 8 further illustrates how the retaining member 40 may be deployed from the stoma tube 22 by introduction of an inflation fluid, represented by arrow 70, through the inflation connector 32 and the inflation line 48. As the inflation fluid enters the retaining member 40, it is forced out of the central bore 42 of the stoma tube 22 until, as shown in FIG. 9, the retaining member 40 is fully deployed.

Figure 9:
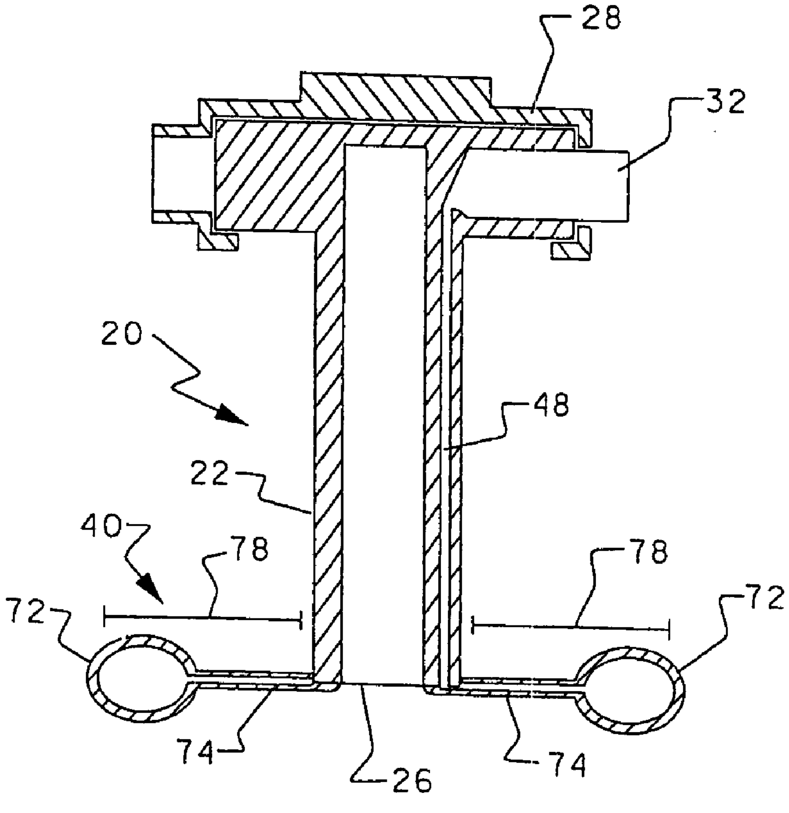
FIG. 9 is a view in lateral cross section of the enterostomy device illustrating the retaining member in a fully deployed position.

FIG. 9 illustrates one exemplar configuration of the retaining member 40 comprising a tubular ring 72 distanced from the distal end 26 of the stoma tube 22 by a skirt 74 of flexible material. The retaining member 40 of the illustrated embodiment provides a low-profile, or flattened ring, configuration which effectively prevents obstruction of the stomach by the retaining member 40, as is frequently experienced with prior devices. Furthermore, it can be seen that the retaining member 40 essentially forms the distal end of the gastrostomy device 20 since the stoma tube 22 does not extend beyond the retaining member 40 as is typically the case in prior devices and, therefore, the retaining member 40 prevents the distal end 26 of the stoma tube 22 from contacting the stomach lining and causing irritation or infection. Additionally, the flattened configuration of the retaining member 40 and the distance 78 with which it extends outward from the stoma tube 22 provide increased surface area for contacting the stomach lining to thereby prevent dislodgement or accidental release of the gastrostomy device 20 from the stoma formed through the patient's body.

Figure 10:
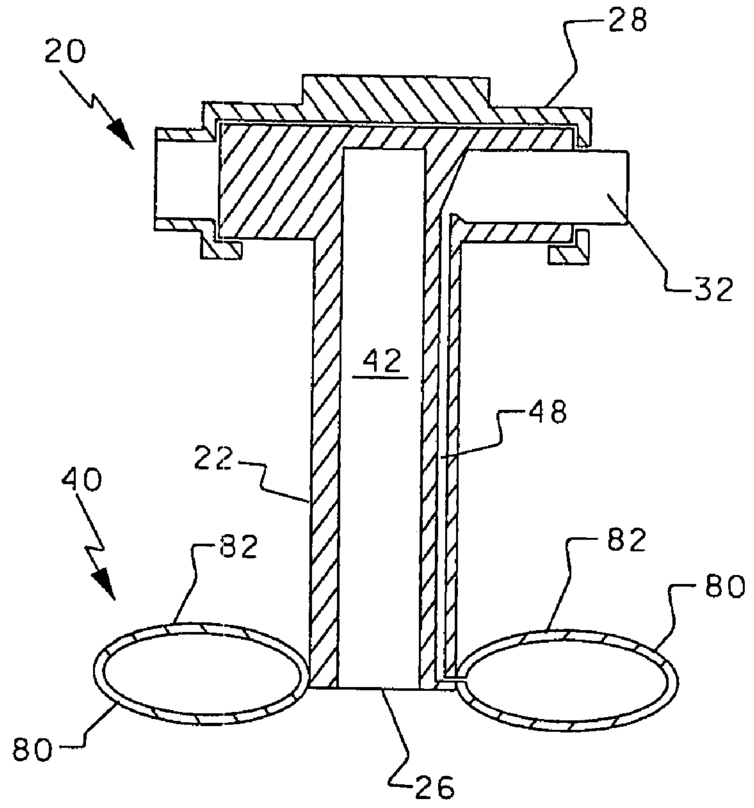
FIG. 10 is a view in lateral cross section of the present invention illustrating an alternative embodiment of the retaining member.
Figure 11:
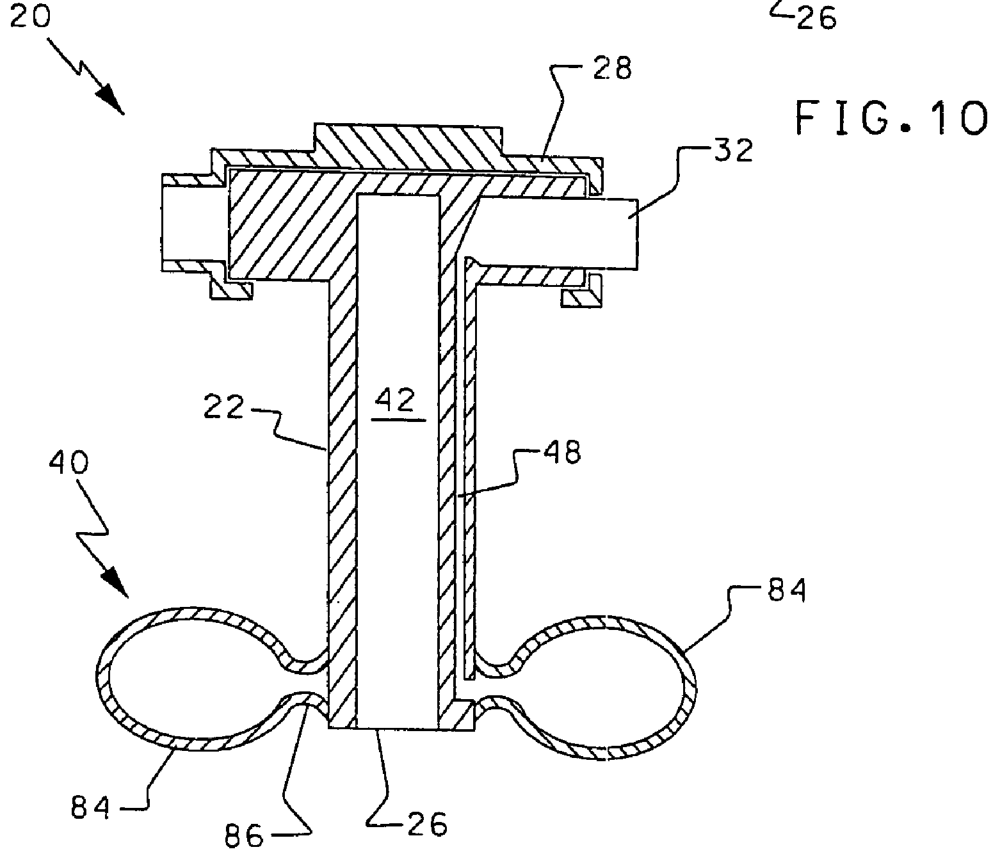
FIG. 11 is a view in lateral cross section of the present invention illustrating another alternative embodiment of the retaining member.

Alternative embodiments of the retaining member 40 which provide a similar flattened configuration with increased surface area are shown in FIGS. 10 and 11. In FIG. 10, the retaining member 40 is formed as a flattened toroidal ring 80 which encircles the distal end 26 of the stoma tube 22. The flattened ring 80 is filled with fluid (i.e., gas or liquid) through the inflation line 48 as previously described and provides a flattened top surface 82 for contacting against the stomach lining of the patient. The extension of the flattened ring 80 from the stoma tube 22 ensures that the gastrostomy device will not become dislodged from the stoma formed through the patient. Similarly, FIG. 11 illustrates another alternative embodiment of the retaining member 40 comprising a toroidal ring 84 of less flattened dimension, but which still provides increased surface area for contacting the stomach lining. The toroidal ring 84 of the illustrated embodiment is distanced from the stoma tube 22 by an inflated collar 86 of flexible material.

The retaining member 40 of the present invention is preferably made from a flexible, biocompatible material, such as silicone or other suitable material, which not only enables the retaining member 40 to be collapsed to a smaller dimension for positioning within the stoma tube 22 prior to deployment, but renders the retaining member 40 compatible to the environment of the stomach. By its architecture and composition, the retaining member 40 prevents epithelialization or similar attempts by the body to incorporate the retaining member 40 into the surrounding tissue. Incorporation is principally prevented as a result of the rounded configuration of the inflatable ring 72 (FIG. 9) or toroidal ring 84 (FIGS. 10 and 11) of the retaining member 40.

Figure 12A:
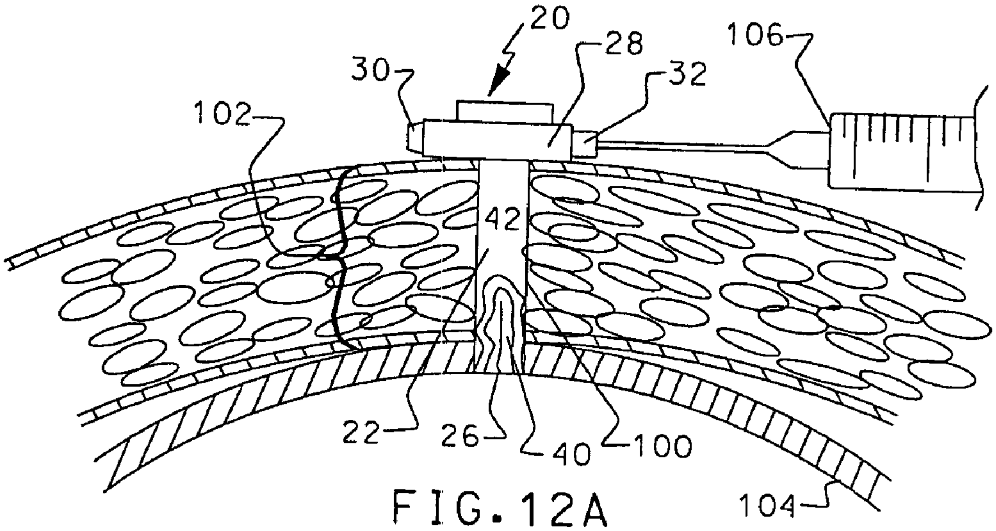
FIG. 12A is a view in partial cross section illustrating initial insertion of the enterostomy device of the present invention into a pre-existing stoma.
Figure 12B:
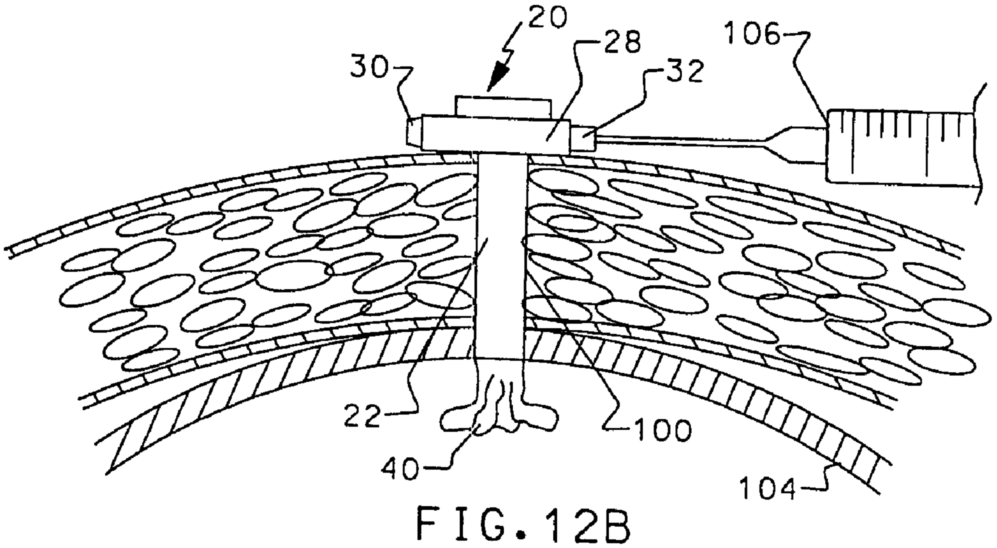
FIG. 12B is a view in partial cross section illustrating partial deployment of the enterostomy device, in the form of a gastrostomy device, in a patient's abdomen.
Figure 12C:
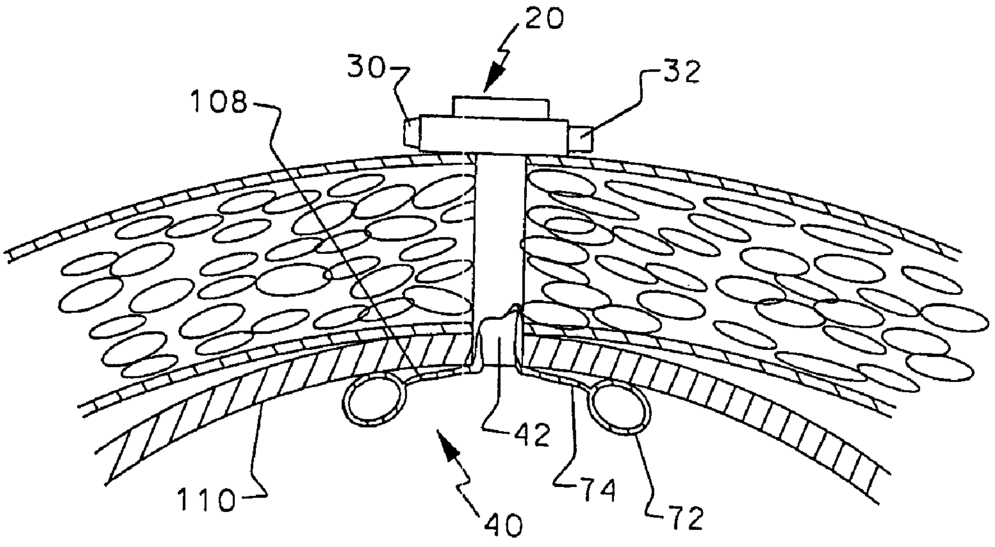
FIG. 12C is a view in partial cut away illustrating full deployment of the enterostomy device in a patient's abdomen.

FIGS. 12A, 12B and 12C illustrate the sequential steps of inserting and deploying the gastrostomy device 20 of the present invention in the stomach of a patient. Deployment is initiated by providing the gastrostomy device 20 in a pre-deployment mode, as previously described and illustrated in FIGS. 1-11. The stoma tube 22 is positioned through an existing stoma 100 formed through the abdominal wall 102 of a patient, as illustrated in FIG. 12A. Because the present invention is designed for insertion in a pre-existing stoma, and because the formation of a stoma is a well-known procedure in the medical arts, the process for forming a stoma will not be discussed herein. The stoma tube 22 is inserted through the stoma 100 until the distal end 26 of the stoma tube 22 is within the environment of the patient's stomach 104. A fluid delivery device 106, such as a syringe, is positioned within the inflation connector to open the valving mechanism therein, and a fluid, such as a gas or saline liquid, is injected into the inflation line 48 of the stoma tube 22. As the fluid moves through the inflation line 48, the retaining member 40 is forced out of the central bore 42 of the stoma tube 22 and into the environment of the stomach 104, as illustrated in FIG. 12B.

When sufficient fluid pressure is achieved to inflate the retaining member 40, as illustrated in FIG. 12C, the fluid delivery device 106 is withdrawn from the inflation connector 32 thereby disabling the valving mechanism and maintaining fluid pressure within the retaining member 40. It can be seen from FIG. 12C that a contact surface area 108 is defined by the skirt 74 and inflated ring 72 of the retaining member 40 which contacts the lining 110 of the stomach to anchor the gastrostomy device 20 in place. In can also be seen that the configuration of the retaining member 40 provides a low-profile which does not obtrusively extend into the interior of the stomach 104 as prior devices do. It can also be seen that the retaining member 40 flexibly conforms to the curvature of the stomach 104 while still maintaining a generally perpendicular orientation to the axis of the stoma tube 22. FIG. 12C illustrates the gastrostomy device in full deployment within the stomach 104, ready for injection of fluids or nutrients through the central bore 42 of the stoma tube 22 and into the stomach, although the port 30 is shown in a closed position.

The enterostomy device 10 of the present invention may also be configured for use as a jejunostomy device 120, as illustrated in FIGS. 13 and 14, which illustrates deployment of the jejunostomy device 120 into the intestine 122 of a patient. As illustrated more particularly in FIG. 13, the jejunostomy device 120 of the present invention is comprised of a stoma tube 22, a rotatable port hub 28 and a retaining member 40 as previously described with respect to the gastrostomy device illustrated in FIGS. 1-11. Similarly, the retaining member 40 is housed within the stoma tube 22 prior to deployment. However, the jejunostomy device 120 also includes a jejunostomy tube 126 which, as suggested by the broken lines of FIG. 13, is housed within the stoma tube 22, along with the retaining member 40, prior to deployment.

Deployment of the jejunostomy device 120 proceeds as previously described with respect to the gastrostomy device, including introduction of an inflation fluid through the inflation connector 32 via a fluid delivery device 106, such as a syringe, to promote inflation of the retaining member 40.

During deployment of the retaining member 40, the jejunostomy tube 126 may remain housed within the stoma tube 22. Once the retaining member 40 is fully deployed, the jejunostomy tube 126 may be deployed by injecting a bolus of fluid, such as saline solution, through the port 30 and into the inlet 56 to produce sufficient fluid pressure in the central bore 42 of the stoma tube 22 to eject the jejunostomy tube 126 into the intestine 122. The jejunostomy tube 126 is intended to project downstream into the intestinal tract and provides fluids and nutrients to the intestine.

The enterostomy device of the present invention is configured to provide a low-profile retaining member which, when deployed in the stomach or intestine, does not obstruct the internal space or environment thereof. The retaining member is also structured with sufficient contact surface area to prevent accidental removal or release of the enterostomy device from the stoma, but is flexible enough, when deflated, to easily remove the device from the patient. The enterostomy device of the present invention is also configured with a low-profile port hub which provides access to the stoma tube without the need for bulky tube sets, and without trauma to the stoma formed in the patient. The structure and configuration of the enterostomy device may be varied to provide a gastrostomy or a jejunostomy device, and may be configured in number of ways to achieve the stated objectives of providing fluids and nutrients to the stomach or intestine of the patient, and venting of the stomach or intestine. Hence, reference herein to specific details of the illustrated embodiments is by way of example and not by way of limitation. It will be apparent to those skilled in the art that many additions, deletions and modifications to the illustrated embodiments of the invention may be made without departing from the spirit and scope of the invention as defined by the following claims.

What is claimed is:

1. An enterostomy device comprising:

a hollow stoma tube having a first end and a second end;

a port disposed on the first end of the stoma tube and configured for passing fluids therethrough, the port being movable between a first position wherein fluid may be injected into but not withdrawn from the stoma tube, a second position wherein fluid may be withdrawn from but not injected into the stoma tube, and a third position wherein the port is not in fluid communication with the stoma tube;

an inflatable retaining member, the inflatable retaining member being attached to the stoma tube adjacent the second end of the stoma tube such that the inflatable retaining member is spaced apart from the stoma tube and wherein the inflatable retaining member is spaced apart from the stoma tube by an noninflatable skirt of material; and an inflation line disposed along the stoma tube and in fluid communication with the inflatable retaining member.

2. The enterostomy device of claim 1, wherein the inflatable retaining member is an inflatable ring.

3. The entersotomy device of claim 1, wherein the inflatable retaining member is connected to the stoma tube via a generally planar connecting member.

4. The enterostomy device of claim 3, wherein the connecting member is not inflatable.

5. The enterostomy device according to claim 1, wherein the port is movable between a first position wherein fluid may enter but not exit from the stoma tube, a second position whereby fluid may exit but not enter the stoma tube, and a third position which prevents the flow of fluid through the stoma tube.

6. The enterostomy device of claim 5, wherein the device further comprises a plurality of valves, one valve of said plurality of valves being disposed in communication with the first position for allowing fluid flow into the stoma tube while inhibiting flow out of the stoma tube into the port, another valve of said plurality of valves being disposed in communication with the second position for allowing fluid flow out of the stoma tube and into the port while inhibiting fluid flow from the port into the stoma tube.

7. The enterostomy device of claim 1, wherein the device further comprises a plurality of valves for selectively allowing flow of fluid from the port into the stoma tube and from the stoma tube into the port while preventing the opposite flow.

8. An entersotomy device comprising:

a stoma tube having a first end and a second end;

a port disposed on the first end of the stoma tube and configured for passing fluids therethrough, the port being movable between a first position wherein fluid may be injected into but not withdrawn from the stoma tube, a second position wherein fluid may be withdrawn from but not injected into the stoma tube, and a third position wherein the port is not in fluid communication with the stoma tube; and wherein the port comprises:

a center portion having a first passage and a second passage, the first and second passages being disposed in fluid communication with the bore of the stoma tube; and an outer portion, the outer portion being movable relative to the center portion and having the port disposed thereon;

an inflatable retaining member disposed adjacent the second end of the stoma tube; and an inflation line disposed along the stoma tube and configured for inflation of the inflatable retaining member.

9. The enterostomy device of claim 8, wherein moving the port to the first position aligns the port with the first passage and wherein moving the port to the second position aligns the port with the second passage.

10. The enterostomy device of claim 8, wherein the first passage comprises a one-way valve configured for allowing fluid to move into the bore of the stoma tube and the second passage comprises a one-way valve configured for allowing fluid to move out of the bore of the stoma tube.

11. The enterostomy device of claim 8, wherein then inflatable retaining member is attached to the stoma tube via a connecting member.

12. The enterostomy device of claim 11, wherein the connecting member comprises a generally planar and flexible material.

13. The enterostomy device of claim 11, wherein the connecting member is uninflatable.

14. The enterostomy device of claim 8, wherein the port is substantially perpendicular to the stoma tube.

15. The enterostomy device of claim 8, wherein the device further comprises a plurality of valves, one valve of said plurality of valves being disposed in communication with the first position for allowing fluid flow into the stoma tube while inhibiting flow out of the stoma tube into the port, another valve of said plurality of valves being disposed in communication with the second position for allowing fluid flow out of the stoma tube and into the port while inhibiting fluid flow from the port into the stoma tube.

16. An enterostomy device comprising:

a stoma tube having a first end and a second end;

a port disposed in fluid communication with the first end and configured for the passage of fluid through the stoma tube;

a retaining member connected to the stoma tube, the retaining member having a first portion and a second portion, wherein the first portion is generally non-inflatable and wherein the retaining member has a first end which is connected to the stoma tube and a second end, and wherein the second portion is inflatable and is connected to the second end of first portion; and an inflation tube disposed along the stoma tube and configured for inflating the second portion of the retaining member.

17. The enterostomy device of claim 16, wherein the first portion of the retaining member comprises a sheet of flexible material.

18. The enterostomy device of claim 16, wherein the second portion of the retaining member comprises a ring.

19. The enterostomy device of claim 16, wherein the port is movable between a first position wherein fluid may be introduced into the stoma tube but not withdrawn, a second position wherein fluid may be withdrawn from the stoma tube but not introduced, and a third position wherein fluid flow through the stoma tube is inhibited.

20. An enterostomy device comprising:

a stoma tube having a first end and a second end;

a port configured for the transmission of fluids into and out of the first end of the stoma tube;

an inflatable retaining member disposed proximate the second end of the stoma tube and connected to the stoma tube via a skin; and an inflation line disposed along the stoma tube, the inflation line extending between the first end of the stoma tube and along the skirt so as to be in fluid connection with the inflatable retaining member.

21. The enterostomy device of claim 20, wherein the inflatable retaining member is attached to the second end of the stoma tube.

22. The enterostomy device of claim 20, wherein the skin is uninflatable.

23. The enterostomy device of claim 20, wherein the port is movable between a first position wherein fluid may be introduced into but not withdrawn from the stoma tube, a second position wherein fluid may be withdrawn from but not introduced into the stoma tube, and a third position wherein fluid flow through the stoma tube is inhibited.

24. The enterostomy device of claim 23, wherein the device further comprises a plurality of valves, one valve of said plurality of valves being disposed in communication with the first position for allowing fluid flow into the stoma tube while inhibiting flow out of the stoma tube into the port, another valve of said plurality of valves being disposed in communication with the second position for allowing fluid flow out of the stoma tube and into the port while inhibiting fluid flow from the port into the stoma tube.

25. An enterostomy device comprising:

a stoma tube having a first end and a second end;

a port configured for the transmission of fluids through the stoma tube;

a plurality of valves disposed in communications with the port and the stoma tube for selectively choosing between allowing flow from the port into the stoma tube and allowing flow from the stoma tube into the port while preventing the opposite flow;

an inflatable retaining member disposed adjacent the second end of the stoma tube and wherein the inflatable retaining member is spaced apart from the stoma tube by an noninflatable skirt of material; and an inflation line disposed along the stoma tube, the inflation line extending to the second end of the stoma tube and configured for inflation of the inflatable retaining member.

* * * * *